United States Patent [19]

Hurd

[11] Patent Number: 4,732,656
[45] Date of Patent: Mar. 22, 1988

[54] APPARATUS AND PROCESS FOR RESOLVING SAMPLE SPECIES

[75] Inventor: Stanley M. Hurd, Hamden, Conn.

[73] Assignee: Bios Corporation, New Haven, Conn.

[21] Appl. No.: 37,209

[22] Filed: Apr. 10, 1987

Related U.S. Application Data

[63] Continuation-in-part of Ser. No. 791,605, Oct. 25, 1985, Pat. No. 4,670,119.

[51] Int. Cl.$^4$ ............................................. G01N 27/28
[52] U.S. Cl. .................... 204/182.4; 204/183.1; 204/299 R
[58] Field of Search ............... 204/183.2, 299 R, 301, 204/183.1, 182.4, 182.9

[56] References Cited

U.S. PATENT DOCUMENTS

| | | | |
|---|---|---|---|
| 3,847,773 | 11/1974 | Snyder | 204/183.1 |
| 4,219,395 | 8/1980 | Smith | 204/183.2 |
| 4,315,812 | 2/1982 | Karlson | 204/183.2 |
| 4,390,403 | 6/1983 | Batchelder | 204/183.1 |
| 4,401,538 | 8/1983 | Hausfeld | 204/183.2 X |

*Primary Examiner*—Donald R. Valentine
*Attorney, Agent, or Firm*—Bachman & LaPointe

[57] ABSTRACT

The apparatus and process of the present invention resolves sample species in an electrolyte solution containing two or more types of ions, wherein the sample species to be resolved will move in response to fluid flow of the electrolyte and a non-linear voltage gradient such that the non-linear voltage gradient serves to counteract forces of diffusion as the sample travels along the electrophoresis chamber good resolution is obtained in species of widely divergent electrophoretic mobility.

12 Claims, 8 Drawing Figures

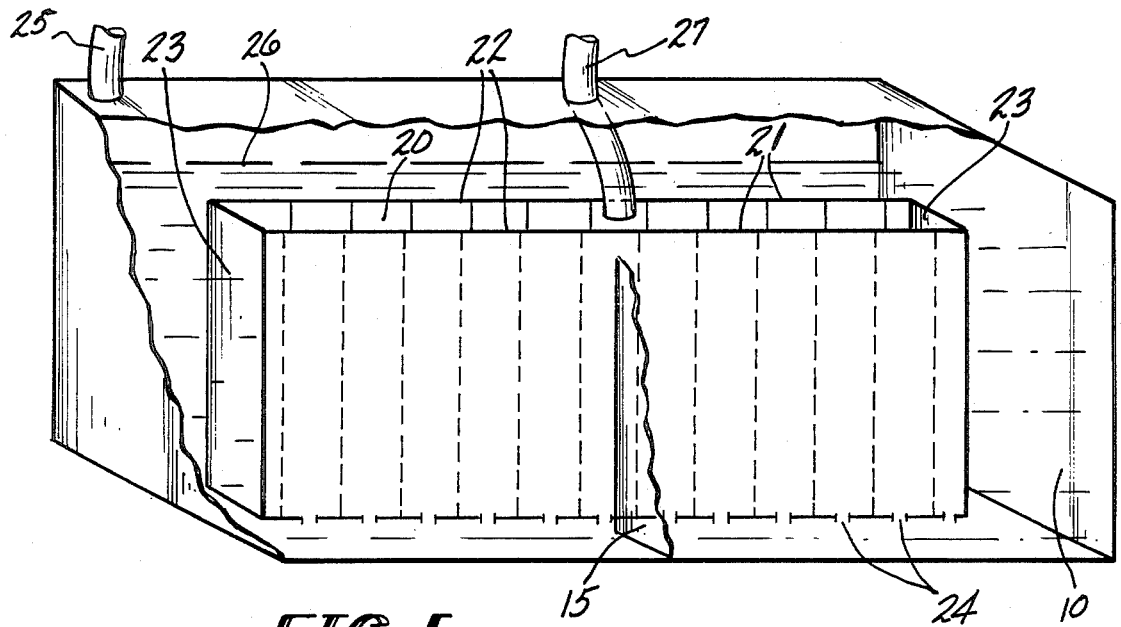
FIG-5
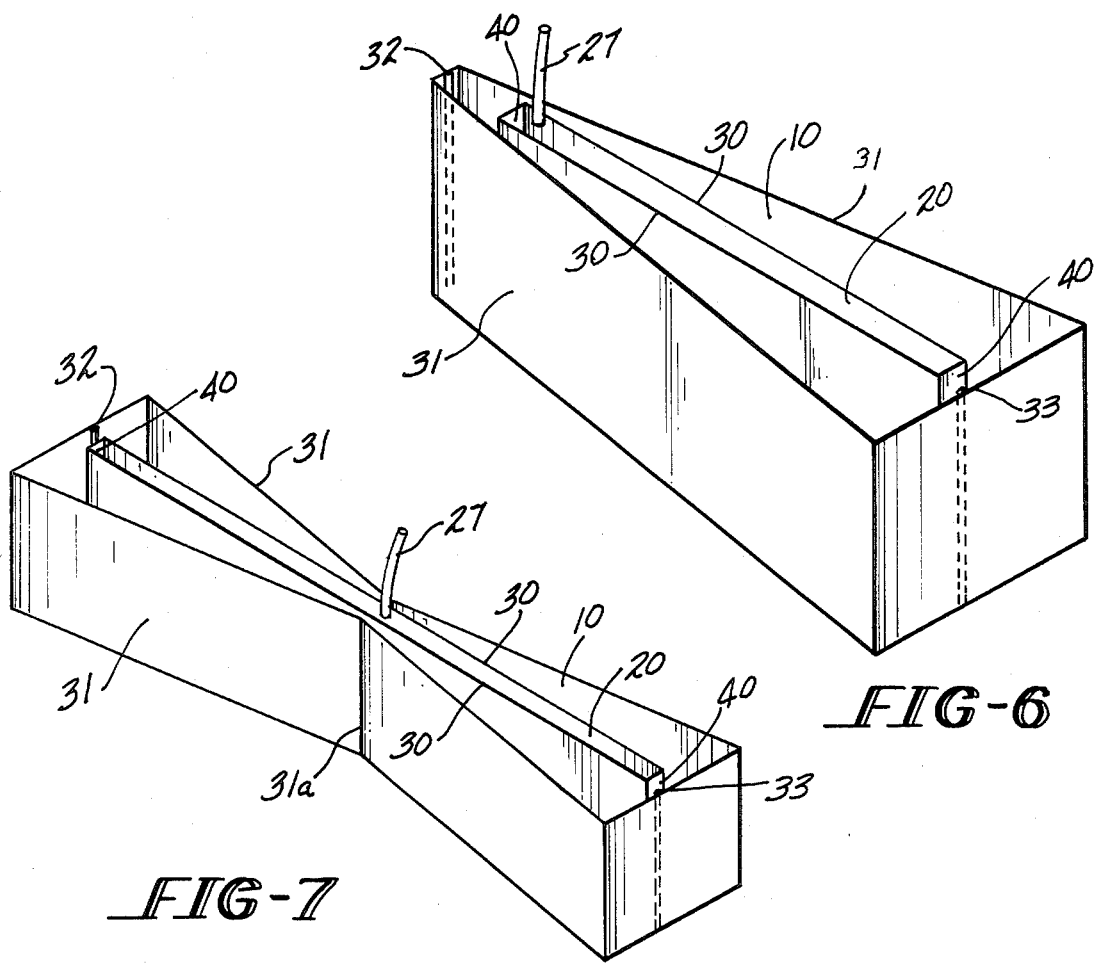
FIG-6
FIG-7

APPARATUS AND PROCESS FOR RESOLVING SAMPLE SPECIES

CROSS-REFERENCE TO RELATED APPLICATIONS

This application is a continuation-in-part of copending U.S. patent application Ser. No. 791,605, for Isoelectric Focusing Device and Process by Stanley M. Hurd, filed Oct. 25, 1985, now U.S. Pat. No. 4,670,119.

BACKGROUND OF THE INVENTION

As is well known in the literature, continuous-flow or "curtain" electrophoresis is an electrokinetic separation technique which utilizes both an electric field and a fluid flow perpendicular to that field to cause a continuous flow of electrolytes to separate on the basis of their charge-to-mass ratios (see, e.g., Deyl, Z., *Electrophoresis: A Survey of Techniques and Applications*, p. 261, Elsevier Scientific Publishing Co., New York, 1979). There are a number of problems associated with this technique, but perhaps the most serious shortcoming is the fact that the species which travel the farthest tend to become more diffuse as they move along the path of the electric field. The end result is that those species which should have the greatest resolution, i.e., those with the greatest electrophoretic mobility, actually lose resolution due to the effects of diffusion.

The aforesaid copending U.S. patent application Ser. No. 791,605 now U.S. Pat. 4,670,119 resides in an apparatus and process for isoelectric focusing which comprises: confining an electrolyte solution in a focusing chamber having an anode end and a cathode end; establishing an electric current through said solution; and providing a plurality of electrode pairs bordering said focusing chamber and applying a non-linear voltage gradient to the electrode pairs along the length of the focusing chamber, whereby the ionic species present in said electrolyte will be concentrated at either the anode or cathode end thereby establishing a steady-state pH gradient in said focusing chamber. It would be highly desirable to utilize features of the aforesaid copending application Ser. No. 791,605 in order to improve sample resolution in an electrophoresis chamber wherein the samples have divergent electrophoretic mobility, and even widely divergent electrophoretic mobility.

It is, therefore, an object of the present invention to provide a novel electrophoretic separation technique which will sort a mixture of macromolecules, such as serum proteins, DNA fragments, enzymes or the like, on the basis of their electrophoretic mobilities.

It is a further object of the present invention to allows such separation to be made in a continuous flow-through fashion.

It is another object of the present invention to provide a means by which the electric field may be configured to counteract the forces of diffusion during the separation run, such that species being resolved do not show the normal tendency to lose resolution as they travel farther along the path of the electric field.

It is a further object of the present invention to provide an apparatus and process which achieves the objectives as aforesaid utilizing features described in said copending U.S. patent application Ser. No. 791,605 now U.S. Pat. No. 4,670,119 and allowing maximum flexibility in the selection of the voltage gradient through the array of electrode pairs described therein.

It is a still further object of the present invention to provide an apparatus and process as aforesaid which is simple and convenient to use.

Further objects and advantages of the present invention will appear hereinbelow.

SUMMARY OF THE INVENTION

In accordance with the present invention the foregoing objects and advantages may be readily obtained.

The apparatus of the present invention resolves sample species in an electrolyte solution containing two or more types of ions. The apparatus comprises: an electrolyte; a continous electrophoresis chamber containing said electrolyte having a long axis, an upper portion and a lower portion; means, preferably a plurality of electrode pairs bordering on said electrophoresis chamber to establish a non-linear voltage gradient therein; means for obtaining fluid flow of said electrolyte in said electrophoresis chamber from the upper portion to the lower portion; and means for injecting a sample species to be resolved into a single upper portion of said electrophoresis chamber wherein sample species to be resolved will move in response to said fluid flow and non-linear voltage gradient such that the non-linear voltage gradient serves to counteract forces of diffusion as the sample species travel along said chamber and wherein good resolution is obtained in species of widely divergent electrophoretic mobility.

The process of the present invention comprises: confining an electrolyte solution in a continuous electrophoresis chamber having a long axis, an upper portion and a lower portion; establishing a non-linear voltage gradient in said electrolyte solution preferably using a plurality of electrode pairs bordering thereon; providing fluid flow of said electrolyte in said electrophoresis chamber from the upper portion to the lower portion; and injecting a sample species to be resolved into a single upper portion of said electrophoresis chamber whereby sample species to be resolved will move in response to said fluid flow and non-linear voltage gradient such that the non-linear voltage gradient serves to counteract forces of diffusion as the sample species travel along said chamber and whereby good resolution is obtained in species of widely divergent electrophoretic mobility.

The present invention utilizes a non-linear voltage gradient. The present invention may be more readily understood by considering the example of an exponentially decreasing voltage gradient. A cationic species injected into the fluid-flow at the anode end of the chamber will begin to move toward the cathode. As a result of the non-linear field, those molecules closest to the anode end will experience a steeper voltage gradient than those closest to the cathode end. Therefore, the trailing edge of the sample (toward the anode end) will always be moving faster than the leading edge (toward the cathode end). Therefore, the sample band will experience a continual sharpening effect which will tend to counter the effects of diffusion. The present invention uses features of the aforesaid copending U.S. patent application Ser. No. 791,605, now U.S. Pat. 4,670,119 the disclosure of which is hereby incorporated by reference, in order to improve sample resolution in an electrophoresis chamber. The present invention also describes a novel process and apparatus to achieve such benefits, having the additional benefits of low cost and simplicity of operation. An embodiment of the present invention preferably utilizes an electrophoresis chamber having side walls disposed such that the width of the chamber varies along the length of the chamber. An internal channel is placed within the chamber and is constructed of a material such as dialysis membrane sheets, which will allow electric field lines to pass freely through them, yet will retain the species being resolved. In this fashion, the field density, and therefore the voltage gradient, will vary along the length of the sample channel in a manner consistent with the process described herein. Variable configuration chambers have been described previously in isoelectric applications see, for example, U.S. Pat. No. 4,401,538, but the present use of non-linear fields in order to sharpen resolution, especially in a flow-through application, represents a considerable advantage.

BRIEF DESCRIPTION OF THE DRAWINGS

For a fuller understanding of the present invention described herein, reference should be made to the accompanying drawings, wherein.

FIG. 5 is a representative apparatus of the present invention showing a preferred embodiment utilizing a plurality of electrode pairs to establish and maintain the desired voltage gradient, seen in an oblique view from above with the front wall removed for clarity;

FIG. 6 is a schematic representation seen in an oblique view from above of an alternate embodiment of the present invention, in which non-parallel side walls are used to establish a non-linear voltage gradient;

FIG. 7 is a schematic representation seen in an oblique view from above of an alternate embodiment of the present invention, in which non-parallel sides of more complicated shapes are used to establish a non-linear voltage gradient; and, FIG. 8 is a schematic representation of the voltage gradient which would be established in the embodiment of FIG. 7.

DETAILED DESCRIPTION

Figure 1:
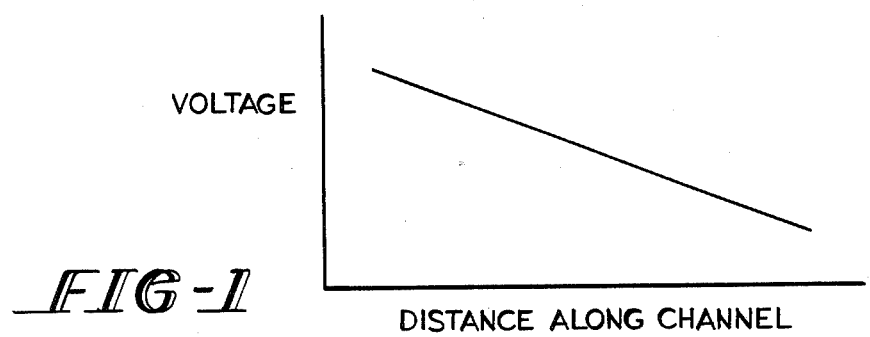
FIG. 1 is a schematic representation of a linear voltage gradient.
Figure 2:
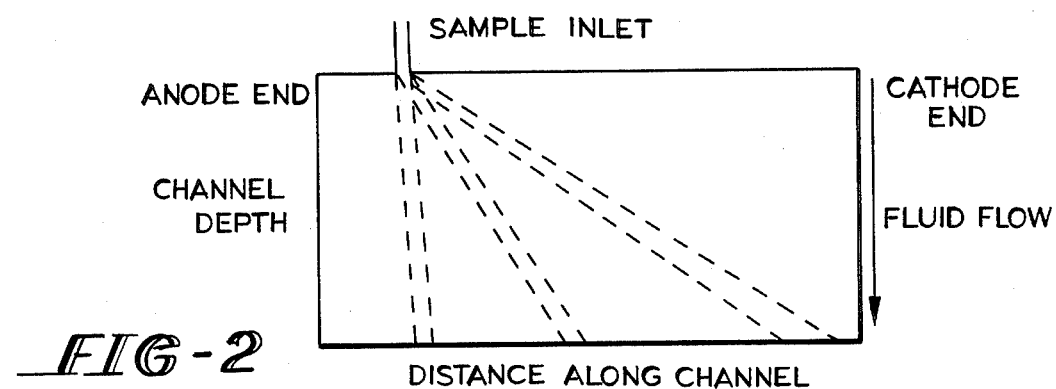
FIG. 2 is a schematic representation of the pathways of several sample species that would result from the application of a voltage gradient of FIG. 1 to a curtain flow electrophoresis apparatus.

The process of non-linear voltage electrophoresis may be understood by referring to FIGS. 1-4. In conventional curtain electrophoresis, a linear voltage gradient is established along the length of a thin, vertically-aligned, rectangular channel, an appropriate fluid, such as a buffer solution, is introduced along the top of the channel, establishing a "curtain" flow that runs perpendicular to the electric field. FIGS. 1-2 illustrate the voltage gradient of such a system and the paths of three different species as they move in response to both the fluid flow and electric fields. As is illustrated in FIG. 2, diffusion tends to broaden the profiles of those species having the longer pathways.

Figure 3:
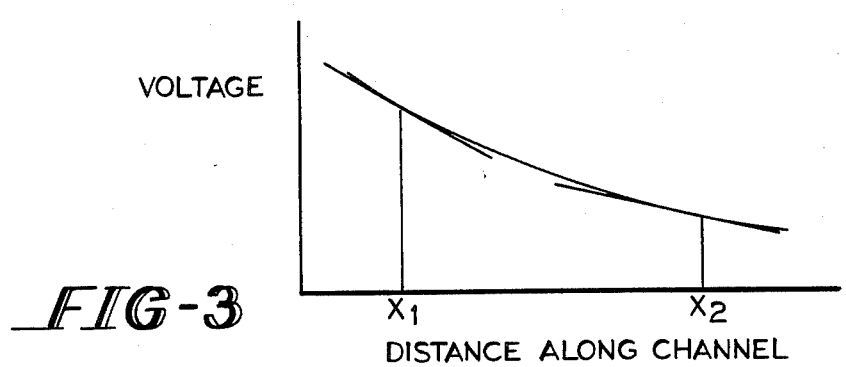
FIG. 3 is a schematic representation of a non-linear voltage gradient.
Figure 4:
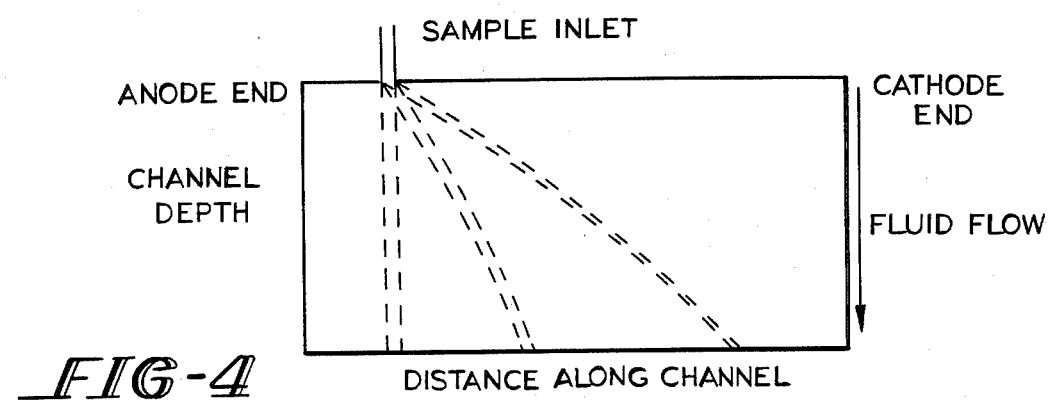
FIG. 4 is a schematic representation of the pathways of several sample species that would result from the application of a voltage gradient of FIG. 3 to a curtain flow electrophoresis apparatus.

FIG. 3 illustrates a non-linear voltage gradient, in this case decreasing exponentially. Two lines are drawn tangent to this gradient at points $X_1$ and $X_2$, indicating the gradients experienced by particles at these points.

As can be clearly seen, the voltage gradient at $X_1$ is steeper than the gradient at $X_2$. This means that a sample species at $X_1$ will be moving more rapidly in the horizontal direction than the same species at $X_2$. This leads to the result that those molecules on the trailing edge of a species elution path will always be moving more rapidly than those on the leading edge. This causes the elution path to become more narrow as the species moves along the voltage gradient. The sample species also tend to move more slowly in aggregate as they reach the swallower portions of the voltage gradient, leading to the elution paths illustrated in FIG. 4.

FIG. 5 shows a preferred embodiment of the invention in an oblique view from the top, with the front wall and sides of reservoir chamber 10 cut away to illustrate electrophoresis channel 20 within the reservoir chamber 10.

Electrophoresis channel 20 is comprised of two side walls 21 constructed of a rigid, inert, insulating material. Along the inner surface of these walls are positioned a series of electrode pairs 22, arranged such that the plane formed between the two members of a pair is orthogonal to the long axis of electrophoresis channel 20. These electrodes may be constructed of conducting materials such as platinum wire or thin linear graphite films. Each electrode pair is electrically connected to a suitable power source to maintain the desired voltage gradient along electrophoresis channel 20. In this embodiment the electrode pairs are equally spaced along the length of electrophoresis channel 20, so that a non-linear voltage gradient applied to them would be accurately reflected by the field lines in the channel, wherein the lines of electric force have a net component parallel to the long axis of the electrophoresis chamber. However, it would also be feasible to use a non-linear spacing in conjunction with a linear voltage gradient to achieve a similar result.

The ends 23 of electrophoresis channel 20 are covered with a material which is permeable to the small electrolytes of the reservoir solution, but which is impermeable to the large species to be resolved in the channel. In a preferred embodiment this material might be dialysis membrane. Electrophoresis channel 20 is thus in electrical and chemical communication with the reservoir solution.

The interior of the channel is in fluid communication with the outside of the apparatus through a series of tubes 24 or other such means disposed along the bottom of the channel. These tubes serve to collect the resolved species and transport them to suitable collection vessels.

In order to reduce convection due to the gas evolved during electrolysis, electrophoresis channel 20 may be lined with an inert, conductive membrane to prevent disruption of the resolved species by said convection. In a preferred embodiment this membrane might be dialysis membrane.

Reservoir chamber 10 is constructed of an inert and non-conductive material. The volume of this chamber must be sufficiently greater than that of electrophoresis channel 20 that the concentration of electrolytes remains essentially constant during the electrophoresis run. It should be supplied with a suitable means of mixing (not shown) so that the anolytes and catholytes produced at the electrodes can be adequately mixed and neutralized, in order to maintain steady-state conditions during the electrophoresis run. It is also supplied with means for reducing the amount of current flowing through reservoir chamber 10 by reducing the cross-sectional area of the reservoir chamber, as by non-conductive baffles 15 which substantially reduce the cross-sectional area of the through which the field lines must pass, thereby reducing the total current being carried by the system.

In operation, a buffer solution is introduced into the top of reservoir chamber 10 via buffer inlet 25 in a uniform fashion by gravity feed or suitable pumping means. Fluid level 26 is for example shown above electrophoresis channel 20 so that the buffer flow is directed in a vertical fashion through channel 20, and it is removed at the bottom by tubes 24 communicating to collection vessels on the outside (not shown). A mixture of species to be separated is introduced into channel 20 as by means of sample inlet 27. The rate of sample flow is less than or equal to that of the curtain buffer, so that the narrow profile of the sample stream is maintained. As the sample species move downward with the flow of the curtain buffer, they also move horizontally in response to the applied electric field. In an exponentially decreasing voltage gradient, these two perpendicular movements lead to the type of elution profile shown in FIG. 4.

There is another manner in which a non-linear voltage gradient may be established in an electrolyte solution. As is well known in the art, field lines in an electrolyte solution contained in a non-conductive vessel will conform to the shape of the vessel (see Harnwell, G. P., Principles of Electricity and Electromagnetism, McGraw-Hill Publishing Co., New York, 1949). If the vessel has a uniform cross-section, the field-line density, and therefore the voltage gradient, will also be uniform. However, if the vessel is not of a uniform cross-section, the voltage gradient will vary proportionately to the cross-section area of the vessel.

An alternate embodiment utilizing this principle is illustrated in FIG. 6. In this embodiment, an electrophoresis channel 20, defined by end walls 40 and side walls 30, is constructed of a material which is permeable to the small electrolytes of the reservoir solution, but which is impermeable to the large species to be resolved in the channel. In a preferred embodiment this material might be dialysis membrane. In this way, electrophoresis channel 20 is in electrical and chemical communication with the solution in reservoir chamber 10. The interior of the channel is also in fluid communication with the outside of the apparatus through a series of tubes or other such means disposed along the bottom of the channel (not shown). These tubes serve to collect the resolved species and transport them to suitable collection vessels.

Reservoir chamber 10 is constructed on an inert and non-conductive material. It is constructed such that the cross-sectional area of the chamber varies along its length. In the preferred embodiment illustrated in FIG. 6, the side walls 31 of chamber 10 are linear and are disposed at an angle to each other, with the narrowest end corresponding to the anode end. Anode and cathode means 32 and 33, respectively, are disposed along the ends of chamber 10 at the anode and cathode ends, respectively. Such means may be platinum wire, linear graphite, or other such conducting means. Such an embodiment would give rise to a voltage gradient such as the one illustrated in FIG. 4. Electrophoresis channel 20 is disposed in the center of the reservoir chamber 10 such that the long axis of the channel is parallel to the long axis of the chamber. In this way, the species being resolved move along the length of the channel in response to a continuously varying electric field, giving rise to the benefits described above. The species are introduced into electrophoresis channel 20 through sample injection tube 27 by gravity feed or by suitable pumping means.

Vertical buffer flow may be obtained in this embodiment in the same way as in the embodiment of FIG.

Figure 8:
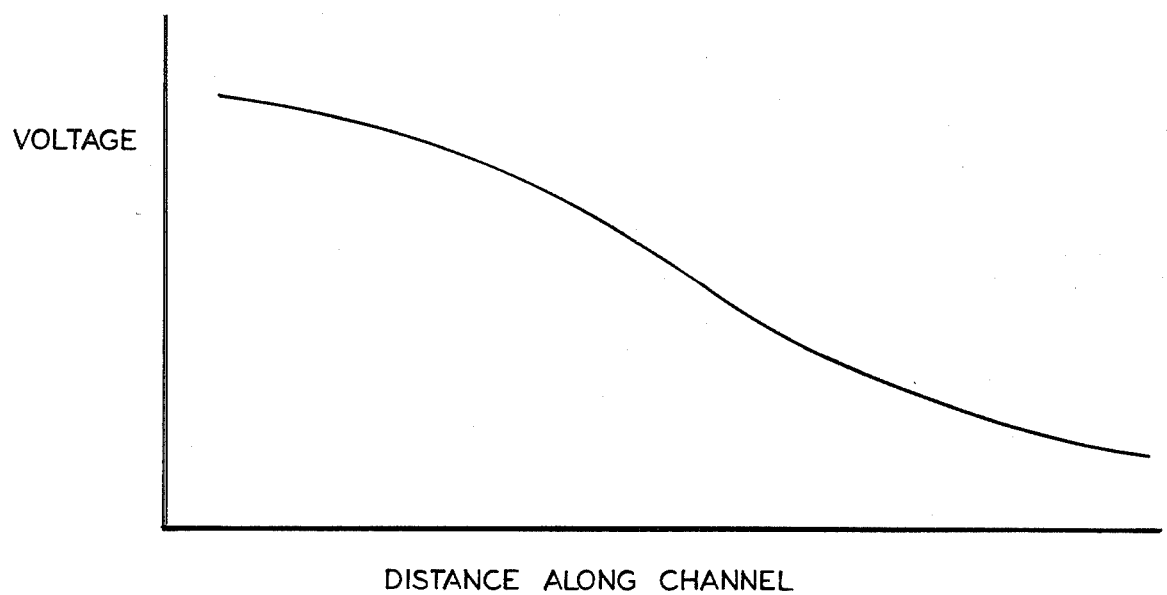

In an alternative embodiment, the side walls of the reservoir chamber may have a more complex shape, such that voltage gradients of any desired configuration may be established by the use of suitable side walls. One such alternate embodiment is illustrated in FIG. 7 wherein side walls 31 have closely spaced central portion 31a with oppositely diverging walls towards the anode and cathode ends 32 and 33, respectively. This embodiment would be particularly efficacious in resolving a mixture of species having either positive or negative charges, with both types being separated under the influence of a non-linear voltage gradient. This may be understood by reference to the voltage gradient resulting from such a configuration, illustrated in FIG. 8. As can be seen, the voltage gradient is sigmoidal in nature. If the mixture of species to be resolved is injected at the inflection point of the gradient (i.e. at the center point of the chamber), those species having negative charges would migrate in the direction of the anode (to the left). In so doing they would initially be moving through a steep portion of the gradient, and as they continued to move they would move through progressively more gentle portions of the curve. Those species having a positive charge would move through a voltage gradient and in a manner similar to that already described for FIG. 4.

This embodiment and that of FIG. 6 offer the benefits of being relatively simple to operate and inexpensive to manufacture when contrasted against the embodiment of FIG. 5. However, they lack the very great flexibility afforded by the embodiment of FIG. 5 in the selection and adjustment of the desired voltage gradient. In addition, the embodiment of FIG. 6, while by far the simplest of the three, would be suitable only for the resolution of mixtures of like-charged species, such as DNA or RNA. The embodiments of FIGS. 5 and 7 would be suitable for the separation of mixtures of both positively- and negatively-charged species, such as is normally found in protein solutions derived from natural sources. Therefore, each embodiment has certain strengths that make it suitable for different separation applications.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

I claim:

1. Apparatus for resolving sample species in an electrolyte solution containing two or more types of ions which comprises: an electrolyte; a continuous electrophoresis chamber containing said electrolyte having a long axis, an upper portion and a lower portion; a plurality of parallel, vertically aligned, spaced-apart electrode pairs with the members of each pair situated on opposite sides of said electrophoresis chamber and bordering said electrophoresis chamber such that the plane formed between each pair is orthogonal to the long axis of the electrophoresis chamber to establish a non-linear voltage gradient in said electrophoresis chamber, wherein the lines of electric force have a net component parallel to the long axis of the electrophoresis chamber; means for obtaining fluid flow of said electrolyte in said chamber from the upper portion to the lower portion; and means for injecting a sample species to be resolved into a single upper portion of said chamber, wherein sample species to be resolved will move in response to said fluid flow and non-linear voltage gradient such that the non-linear voltage gradient serves to counteract forces of diffusion as the sample species travel along said chamber and wherein good resolution is obtained in species of widely divergent electrophoretic mobility.

2. Apparatus according to claim 1 including fluid removal means located at the lower portion of said chamber.

3. Apparatus according to claim 2 including fluid inlet means located at the upper portion of said chamber.

4. Apparatus for resolving sample species in an electrolyte solution containing two or more types of ions which comprises: an electrolyte; a continuous electrophoresis chamber containing said electrolyte having a long axis, an upper portion and a lower portion; means to establish a non-linear voltage gradient in said electrolyte; means for obtaining fluid flow of said electrolyte in said chamber from the upper portion to the lower portion; and means for injecting a sample species to be resolved into a single upper portion of said chamber, wherein sample species to be resolved will move in response to said fluid flow and non-linear voltage gradient such that the non-linear voltage gradient serves to counteract forces of diffusion as the sample species travel along said chamber and wherein good resolution is obtained in species of widely divergent electrophoretic mobility, including an internal channel within the chamber constructed of a material which will allow electric field lines to pass therethrough, but will retain the species being resolved.

5. Apparatus according to claim 4 wherein said chamber includes linear side walls disposed at an angle to each other, wherein said channel has a long axis and the long axis of the channel is parallel to the long axis of the chamber.

6. Apparatus according to claim 5 wherein said side walls have a closely spaced central portion and oppositely diverging side walls.

7. Apparatus according to claim 4 wherein the width of said chamber varies along the length thereof.

8. Process for resolving sample species in an electrolyte solution containing two or more types of ions which comprises: confining an electrolyte solution in a continuous electrophoresis chamber having a long axis, an upper portion and a lower portion; establishing an electric current throughout said solution; and providing a plurality of parallel, vertically aligned, spaced-apart electrode pairs with the members of each pair situated on opposite sides of said electrophoresis chamber and bordering on said electrophoresis chamber such that the plane formed between each pair is orthogonal to the long axis of the focusing chamber; and applying a non-linear voltage gradient along the length of the electrophoresis chamber by means of said electrode pairs wherein the lines of electric force have a net component parallel to the long axis of the electrophoresis chamber; providing fluid flow of said electrolyte in said chamber from the upper portion to the lower portion; and injecting a sample species to be resolved into a single upper portion of said chamber, whereby sample species to be resolved will move in response to said fluid flow and such that the non-linear voltage gradient serves to counteract forces of diffusion as the sample species travel along said chamber and whereby good resolution is obtained in species of widely divergent electrophoretic mobility.

9. Process according to claim 8 including recovering the resolved species.

10. Process according to claim 8 including forming an internal channel within the chamber constructed of a material which will allow electric field lines to pass therethrough, but will retain the species being resolved.

11. Process according to claim 8 including adding electrolyte to the upper portion of said chamber and removing electrolyte from the lower portion of said chamber.

12. Process according to claim 8 including the step of varying the width of said chamber along the length thereof.

* * * * *